United States Patent
Budhabhatti et al.

(10) Patent No.: US 11,419,544 B2
(45) Date of Patent: Aug. 23, 2022

(54) SYSTEMS AND METHODS FOR ANASTOMOSIS LEAKAGE DETECTION AND PREDICTION

(71) Applicant: Covidien LP, Mansfield, MA (US)

(72) Inventors: Sachin Budhabhatti, Unionville, CT (US); Nilay Mukherjee, North Andover, MA (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 16/952,829

(22) Filed: Nov. 19, 2020

(65) Prior Publication Data

US 2021/0204873 A1 Jul. 8, 2021

Related U.S. Application Data

(60) Provisional application No. 62/957,431, filed on Jan. 6, 2020.

(51) Int. Cl.
*A61B 5/00* (2006.01)
*A61B 5/06* (2006.01)
*A61B 6/03* (2006.01)
*A61B 6/12* (2006.01)
*A61B 6/00* (2006.01)
(Continued)

(52) U.S. Cl.
CPC ............ *A61B 5/4848* (2013.01); *A61B 5/062* (2013.01); *A61B 5/7246* (2013.01); *A61B 6/032* (2013.01); *A61B 6/12* (2013.01); *A61B 6/5205* (2013.01); *A61B 8/0833* (2013.01); *A61B 8/5207* (2013.01); *A61B 17/115* (2013.01)

(58) Field of Classification Search
CPC ..... A61B 5/4848; A61B 5/062; A61B 5/7246; A61B 6/5205; A61B 8/0833; A61B 17/115; A61B 17/0644; A61B 2017/00876; A61B 2090/3954; A61B 2505/05; A61B 5/055; A61B 5/064; A61B 6/032; A61B 6/12; A61B 6/5211; A61B 8/0841; A61B 8/5207; A63B 69/205
See application file for complete search history.

(56) References Cited

U.S. PATENT DOCUMENTS

| | | | |
|---|---|---|---|
| 9,295,409 B2 | 3/2016 | Kruglick et al. | |
| 2010/0076429 A1* | 3/2010 | Heinrich | A61B 17/115 606/49 |

(Continued)

FOREIGN PATENT DOCUMENTS

| | | | | |
|---|---|---|---|---|
| EP | 3251603 A1 * | 12/2017 | | A61B 5/066 |
| EP | 3506280 A1 | 7/2019 | | |

OTHER PUBLICATIONS

European Search Report dated Jun. 4, 2021, corresponding to counterpart European Application No. 21150362.8; 9 pages.

*Primary Examiner* — Sean D Mattson
*Assistant Examiner* — Michael Yiming Fang
(74) *Attorney, Agent, or Firm* — Carter, DeLuca & Farrell LLP

(57) ABSTRACT

A system for monitoring anastomosis healing includes an imaging device for observing a first distance at a first location between first and second staple lines at a first instant in time, and a second distance at the first location at a second instant in time, and a programmable device configured to calculate a difference between the first and second distances and to compare the difference with known distances of anastomoses exhibiting known conditions.

16 Claims, 10 Drawing Sheets

(51) Int. Cl.
    *A61B 8/08*           (2006.01)
    *A61B 17/115*       (2006.01)

(56) References Cited

U.S. PATENT DOCUMENTS

| | | | |
|---|---|---|---|
| 2011/0166444 A1* | 7/2011 | Elgort | A61B 17/064 |
| | | | 600/424 |
| 2012/0101363 A1* | 4/2012 | Gordon | A61N 2/02 |
| | | | 600/411 |
| 2013/0150685 A1 | 6/2013 | Toth | |
| 2018/0042528 A1 | 2/2018 | Helwa et al. | |
| 2018/0279925 A1* | 10/2018 | Emmons | A61B 17/07292 |
| 2019/0201136 A1* | 7/2019 | Shelton, IV | A61B 17/0206 |
| 2019/0214127 A1* | 7/2019 | Hu | G16H 50/70 |
| 2021/0212775 A1* | 7/2021 | Shelton, IV | A61B 34/76 |

\* cited by examiner

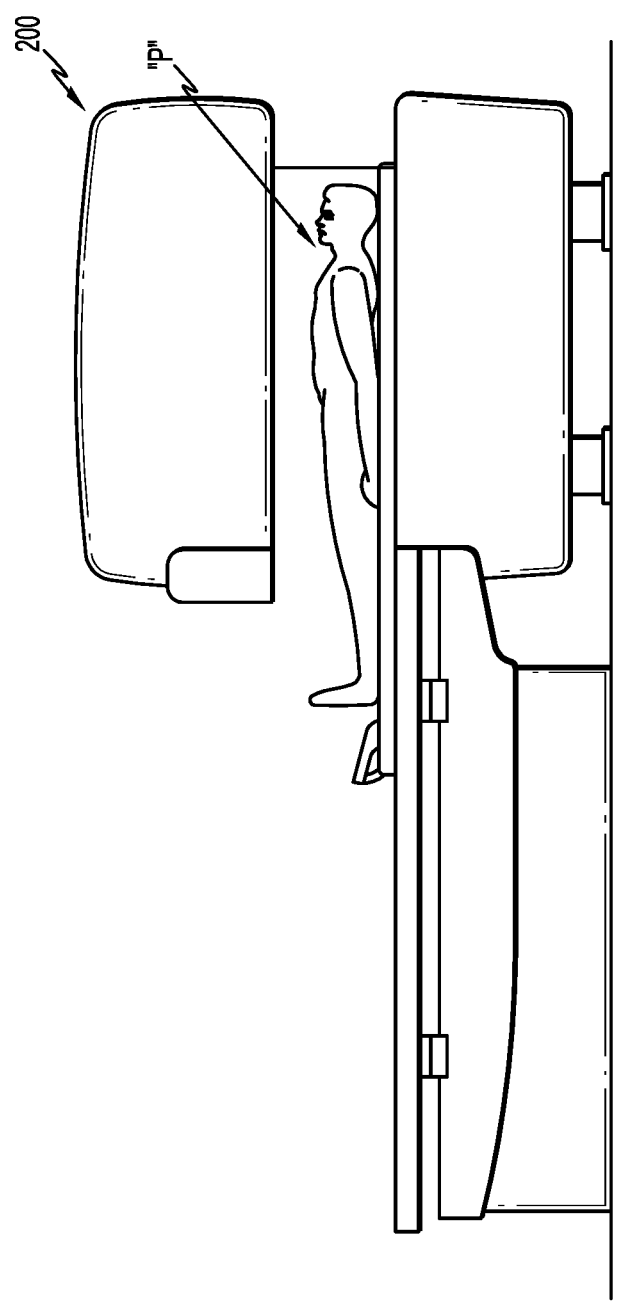

SYSTEMS AND METHODS FOR ANASTOMOSIS LEAKAGE DETECTION AND PREDICTION

CROSS-REFERENCE TO RELATED APPLICATIONS

This application claims the benefit of and priority to U.S. Provisional Patent Application Ser. No. 62/957,431 filed Jan. 6, 2020, the entire disclosure of which is incorporated by reference herein.

FIELD

The present disclosure relates anastomotic leaks. More particularly, the present disclosure relates to devices and methods for detecting and predicting anastomotic leaks.

BACKGROUND

Anastomosis is the surgical joining of separate hollow organ sections. Typically, an anastomosis procedure follows a surgical procedure in which a diseased or defective section of hollow tissue is removed and the remaining end sections are drawn together and joined. Depending on the desired anastomosis procedure, the end sections may be joined by either circular, end-to-end, or side-to-side organ reconstruction methods.

Anastomotic leaks occur due to disruption of the anastomrotic site, which is typically stapled together. In some cases, anastomotic leaks are the result of a disruption of the staple line.

Accordingly, it would be beneficial to have systems and methods for monitoring anastomoses and for detecting leaks and more accurately predicting the probability of leaks.

SUMMARY

A system for monitoring anastomosis healing is provided. The system includes an imaging device and a programmable device. The imaging device observes a first distance at a first location between first and second staple lines at a first instant in time and observes a second distance at the first location at a second instant in time. The programmable device is configured to calculate a difference between the first and second distances and to compare the difference with known distances of anastomoses exhibiting known conditions.

In certain aspects of the disclosure, the known condition includes healthy anastomoses. Alternatively or in addition, the known condition includes anastomoses exhibiting leakage.

In some aspects, the imaging device may be configured for observing a distance between first and second staples within the first staple line. The programmable device may be configured to be worn by a patient. Staples within the first staple line may include a first coating and staples within the second staple line include a second coating different from the first coating. Alternatively, staples within the first staple line may include at least one bead secured thereto.

In aspects of the disclosure, the imaging device uses at least one of x-rays, MRI, CT scan, or ultrasound.

A method of monitoring anastomosis healing is also provided. The method includes: observing a first distance between a first staple line and a second staple line at a first location at a first instant in time; observing a second distance between the first staple line and the second staple line at the first location at a second instant of time; calculating a difference between the first and second distances; comparing the difference between the first and second distances with known values of similar measurements in anastomoses having known conditions; and determining a proper course of treatment based on the comparisons.

In certain aspects of the disclosure, comparing the difference between the first and second distances includes comparing the difference with differences between staple lines of healthy anastomoses at similar instants in time. Comparing the difference between the first and second distances may include comparing the difference with known values of similar measurements of anastomoses experiencing leakage. Observing the first and second distances may include using x-rays, MRI, CT scan, or ultrasound. Calculating the difference between the first and second distances may include using a programmable device.

In some aspects, the method further includes observing a third distance between a first staple and a second staple in the first staple line at a first instant in time, observing a fourth distance between the first staple and the second staple at a second instant in time, and comparing a difference between the third and fourth distances with known values of similar measurements.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the disclosure given below, serve to explain the principles of the disclosure, wherein:

FIG. 7 is a schematic view of an imaging device according to an aspect of the present disclosure;

DETAILED DESCRIPTION

Figure 1:
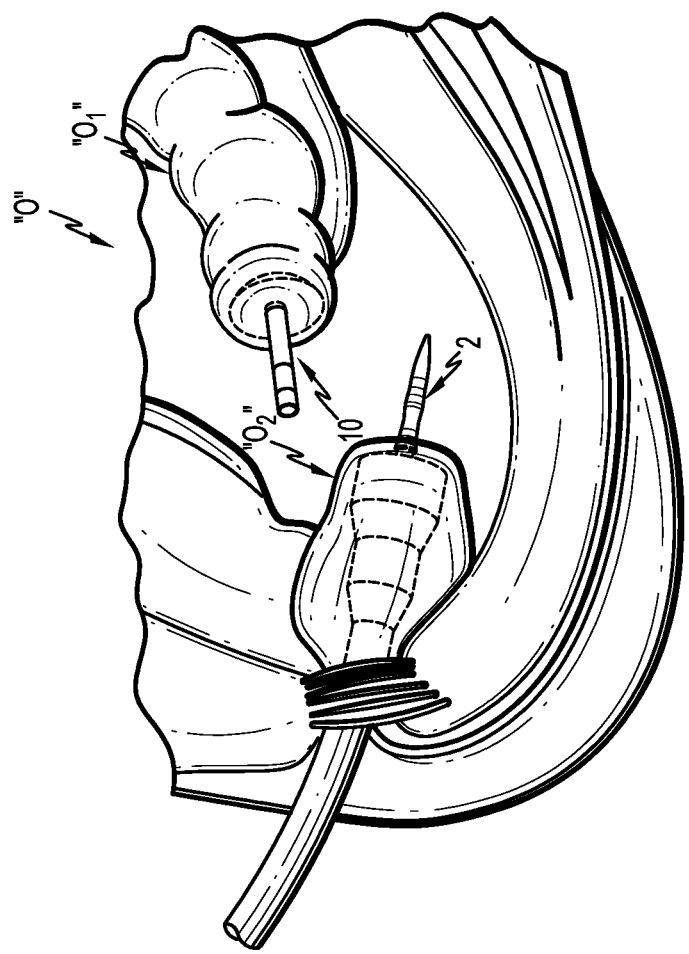
FIG. 1 is a perspective view of a surgical site prior to the completion of an anastomosis procedure.

Aspects of the presently disclosed systems and methods for detecting and/or predicting anastomotic leaks will now be described in detail with reference to the drawings in which like reference numerals designate identical or corresponding elements in each of the several views. As is common in the art, the term "proximal" refers to that part or component closer to the user or operator, e.g. surgeon or clinician, while the term "distal" refers to that part or component farther away from the user.

Figure 2:
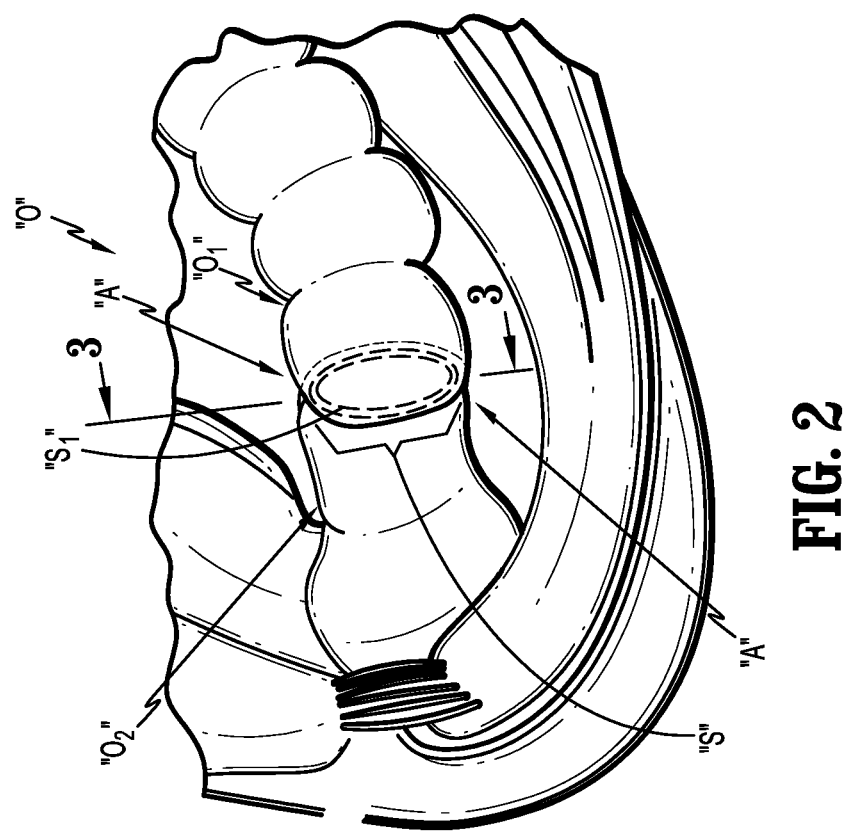
FIG. 2 is a perspective view of the surgical site shown in FIG. 2 subsequent to the completion of an anastomosis procedure.

FIG. 1 illustrates the joining of a first portion "$O_1$" of a tubular organ "O" with a second portion "$O_2$" of the tubular organ "O" in an anastomosis procedure. More particularly, the first portion "$O_1$" of the tubular organ "O" is securable to an anvil assembly 10 and the second portion of the tubular organ "O" is secured to a distal end of an anastomosis device, e.g., a circular stapler 1. The anvil assembly 10 is operably secured to a trocar member 2 extending from a distal end of the circular stapler 1. Approximation of the anvil assembly 10 relative to the distal end of the circular stapler 1 positions the first and second portions "$O_1$", "$O_2$" of the tubular organ "O" relative to each other. Actuation of the circular stapler 1 causes the firing of a plurality of surgical staples "S" through the first and second portions "i", "$O_2$" of the tubular organ "O" to create an anastomosis "A" (FIG. 2).

The anastomosis "A" may include one or more staple lines. As shown and described throughout the disclosure, the anastomosis "A" includes two staple lines; however, in aspects, the anastomosis "A" may include only a single staple line or three or more staple lines. In aspects, the staples in a first staple line are aligned with the staples in a second staple line. Alternatively, the surgical staples in a first staple line may be staggered relative to the surgical staples in a second staple line.

Various systems and methods for monitoring the condition of an anastomosis "A" of the tubular organ "O" throughout the healing process, and for detecting the possibility of leaks and predicting the potential leaks are described hereinbelow. By analyzing properties of the anastomosis quantitatively, and comparing these properties with known values of healthy anastomoses and/or known values of anastomoses experiencing leakage, a healthcare provider may more accurately identify an anastomotic leak and/or the increased potential for an anastomotic leak. In addition, by quantitatively analyzing the anastomosis proprieties, a healthcare provider may also be able to determine the progress of the healing process. The known values may be stored in memory associated with the system.

One method for quantitatively analyzing an anastomosis "A" is through observation of the individual staples and/or the one or more staple lines. More particularly, by observing various properties, e.g., relative position of the staples of the one or more staple lines following an anastomotic procedure and during the healing process, and comparing theses values with known values of staple and/or staple lines in anastomoses having known characteristics, i.e., healed without complications, the healthcare provider may be able to more accurately determine the condition of the anastomosis and/or more accurately predict the potential for leaks.

Figure 3A:
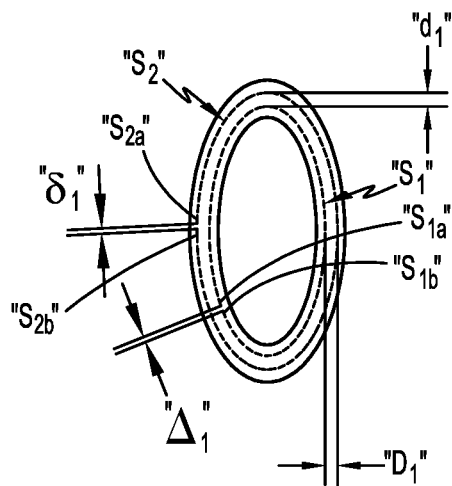
FIG. 3A is a cross-sectional end view of the anastomosis shown in FIG. 2 taken along line 3 shown in FIG. 2 at a first instant in time.

FIG. 3A illustrates a cross sectional view of the anastomosis "A" at a first instant in time following an anastomotic procedure (FIG. 2). The first instant of time may be immediately following the anastomotic procedure or at any subsequent time during the healing process. The first instant in time may be immediately prior to, at a point during, or subsequent to peristalsis or contraction of the tubular organ "O".

As shown, the anastomosis "A" includes a first or inner staple line "$S_1$" and a second or outer staple line "$S_2$". Although shown having an oval cross-sectional shape, it is envisioned that the cross-sectional shape of the anastomosis may instead form a circle, or other shape. At the first instant in time, the first and second staple lines "$S_1$", "$S_2$" are separated by a first distance "$d_1$" at a first location along the first and second staple lines "$S_1$", "$S_2$", and are separated by a second distance "$D_1$" at a second location along the first and second staple lines "$S_1$", "$S_2$". The distance between the first and second staple line "$S_1$", "$S_2$" may be taken at specific locations, as shown, or an average distance between the first and second staple line "$S_1$", "$S_2$" may be calculated.

Quantitative analysis of the anastomosis "A" may further include measuring and monitoring a third distance "$\Delta_1$", for example, between first and second staples "$S_{1a}$", "$S_{1b}$" of the first staple line "$S_1$" at the first instant in time and/or of a fourth distance "$\delta_1$", for example, between first and second staples "$S_{2a}$", "$S_{2b}$" of the second staple line "$S_2$" at the first instant in time.

Figure 3B:
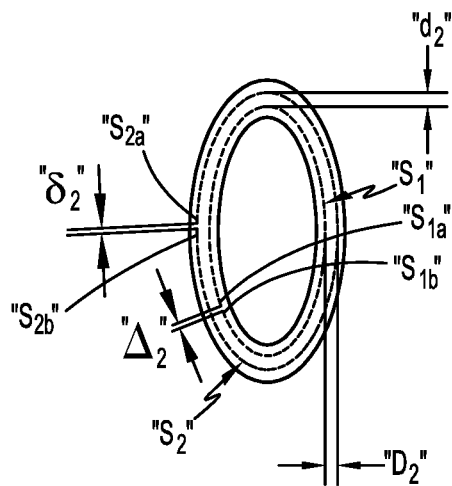
FIG. 3B is the cross-sectional end view shown in FIG. 3A at a second instant in time.
Figure 3C:
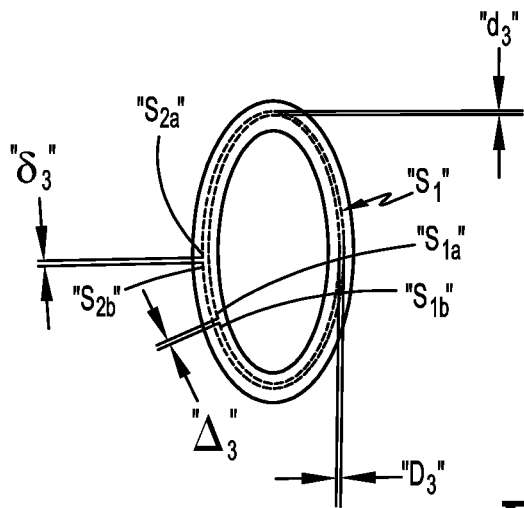
FIG. 3C is the cross-sectional end view shown in FIGS. 3A and 3B at a third instant in time.

FIGS. 3B and 3C illustrate the cross-sectional view of the anastomosis "A" at second and third instants of time, respectively. The second and third instants of time may be during the same stage of peristalsis and/or contraction of the tubular organ "O", at a later time, and/or at different stages of the peristalsis and/or contraction of the tubular organ "O".

Distances "$d_2$", "$d_3$" between the first and second staple lines "$S_1$", "$S_2$" at the first location and distances "$D_2$", "$D_3$" between the first and second staple lines "$S_1$", "$S_2$" at the second location at the respective second and third instants in time may be the same or different than the first distance "$d_1$" at the first location and the second distance "$D_1$" at the second location measured at the first instant in time. By comparing the differences between the distances "$d_1$", "$D_1$" at the first instant in time and the distances "$d_2$", "$D_2$", "$d_3$", "$D_3$" at the second and third instants in time with each other and comparing the differences with known values of the same measurements of properly healing anastomoses and/or anastomoses experiencing leakage, a healthcare provider may more accurately determine the current state of the anastomosis and more accurately predict the likelihood that an anastomotic leak will occur.

A distance "$\Delta_2$", "$\Delta_3$" between the first and second staples "$S_{1a}$", "$S_{1b}$" of the first staple line "$S_1$" and/or a distance "$\delta_2$", "$\delta_3$" between the first and second staples "$S_{2a}$", "$S_{2b}$" of the second staple line "$S_2$" at the second and third instants in time may be the same or different than the distances "$\Delta_1$", "$\delta_1$" between the respective first and second staples "$S_{1a}$", "$S_{1b}$" of the first staple line "$S_1$" and the first and second staples "$S_{2a}$", "$S_{2b}$" of the second staple line "$S_2$" at the first instant in time. As with the distances "$d_1$", "$d_2$", "$d_3$", "$D_1$", "$D_2$", "$D_3$" between the first and second staple lines "$S_1$", "$S_2$" at the respective first and second locations at the first (FIG. 3A), second (FIG. 3B), and third (FIG. 3C) instants in time, respectively, differences in the distances "$\Delta_1$", "$\Delta_2$", "$\Delta_3$" "$\delta_1$", "$\delta_2$", "$\delta_3$" between the respective first and second staples "$S_{1a}$", "$S_{1b}$" of the first staple line "$S_1$" and the first and second staples "$S_{2a}$", "$S_{2b}$" of the second staple line "$S_2$" at the first (FIG. 3A), second (FIG. 3B), and third (FIG. 3C) instants of time, respectively, may be compared with each other and with known values of the same measurements of properly healing anastomoses, and/or anastomoses experiencing leakage, to provide a healthcare provider with a more accurate evaluation of the current state of the anastomosis, and/or to provide for a more accurate prediction of the probability of anastomotic leak.

Observations of staple shedding, i.e., release of the staples during the healing process, may also be used as indicators of normal healing. Indications of normal healing may lead to early patient discharge without extra complications, and reduce the overall cost of medical care to the patient.

Figure 4:
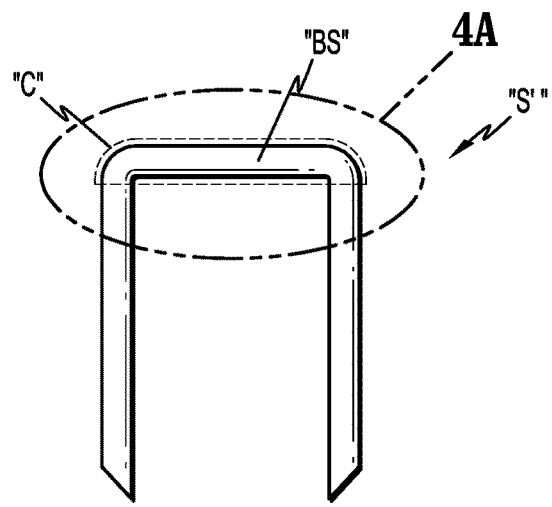
FIG. 4 is a side, view of a surgical staple according to an aspect of the present disclosure.
Figure 5:
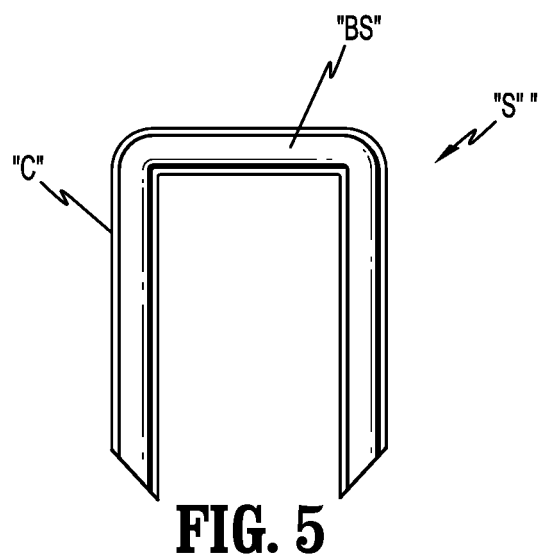
FIG. 5 is a side view of a surgical staple according to another aspect of the present disclosure.
Figure 6:
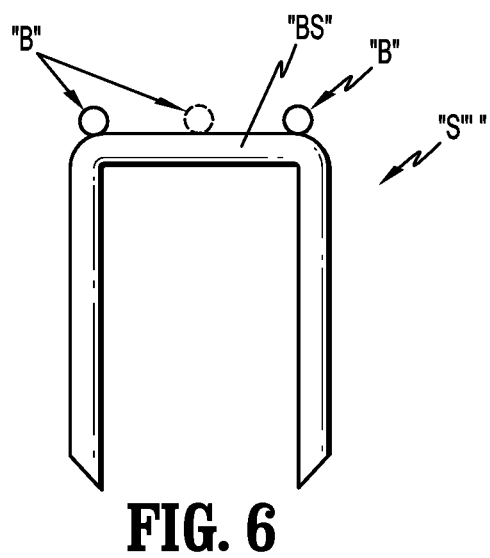
FIG. 6 is a side view of a surgical staple according to yet another aspect of the present disclosure.

FIGS. 4-6 illustrate staples configured to enhance the viewing of first and second staple lines. For example, in one aspect of the disclosure, the surgical staples "S'", "S''" are coated with a ferro-magnetic material "C", e.g., nanomagnet fluid or colloidal magnetic particles suspended in a fluid medium. Some of the surgical staple "S'" (FIG. 4) or all of the surgical staples "S''" (FIG. 5) may be coated with the ferromagnetic material "C" or other coating.

Figure 4A:
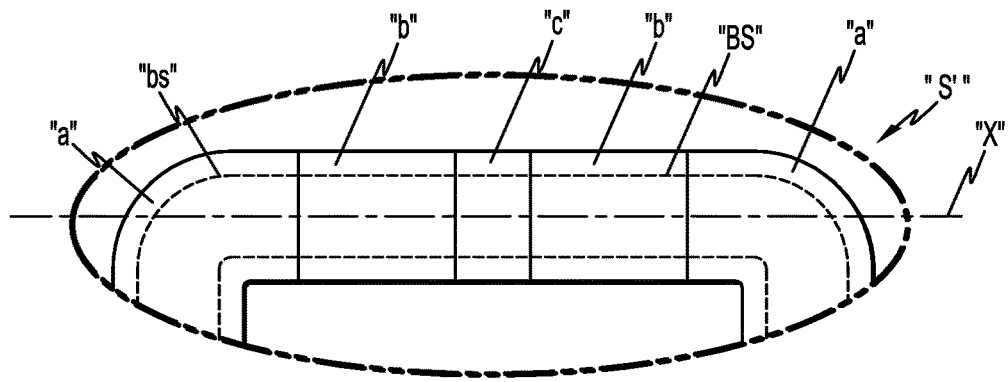
FIG. 4A is an enlarged view of the indicated area of detail shown in FIG. 4.
Figure 4B:
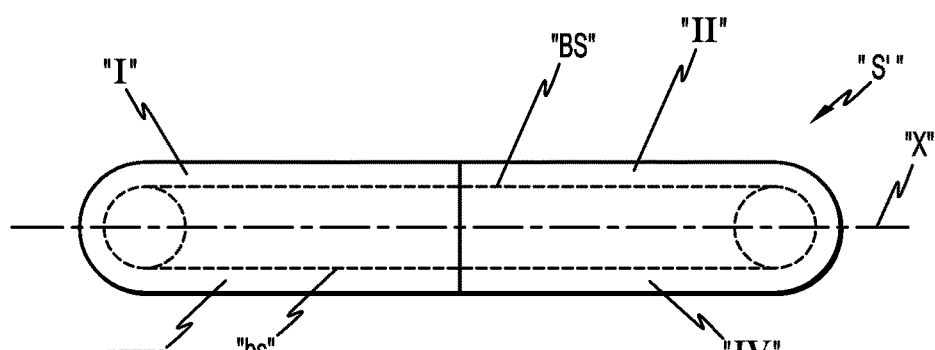
FIG. 4B is a top, perspective view of another aspect of the surgical staple shown in FIG. 4.

FIG. 4A illustrates the backspan "BS" of the surgical staple of FIG. 4, including the coating divided into a plurality of sections along a longitudinal axis "X" of the backspan "BS". In other aspects of the disclosure, and as shown, the coating "C" includes outer sections "a", intermediate sections "b", and a central section "c". FIG. 4B illustrates the backspan "BS" of the surgical staple "S'" of FIG. 4, including a coating "C" divided into a grid. In some aspects of the disclosure, the coating "C" includes a first section "I", a second section "II", a third section "III", and a fourth section "IV". By dividing the coating "C" of the surgical staples "S'" into sections, in addition to observing and monitoring the displacement of the surgical staples "S'" relative to each other, any off-axis or rotational displacement of each individual surgical staples "S'" may also be observed and monitored.

In an alternative aspect of the disclosure, and as illustrated in FIG. 6, one more magnetic beads "B" may be attached to the surgical staple "S''''" to permit external viewing of the staple line. Each of the one or more magnetic beads "B" may be formed of the same or different materials, and may be placed in any suitable arrangement on the backspan "BS" and/or legs of the surgical staple "S''''" to enhance viewing of the surgical staple "S''''".

Following a surgical stapling procedure, the position of the surgical staples "S" in the first staple line "$S_1$" in the tissue forming the anastomosis "A" and the surgical staples "S" in the second staple line "$S_2$" in the tissue forming the anastomosis "A" are observed using known imaging technologies. For instance, the position of the surgical staples "S" may be observed using x-rays, MRI, CT scan, ultrasound or other suitable imaging devices 200 (FIG. 7). The position of the staples "S" may be measured and recorded automatically by the imaging device 200, and/or manually by medical personnel.

As noted above, the measurements of the position of the staples "S" relative to each other and/or the position of the first and second staple lines "S1", "S2" relative to each other taken at the first instant of time may be taken prior to, during, or subsequent to the peristalsis or contraction of the tubular organ "O". The same measurements are then taken at the second instant in time and the difference between the various distances measured at the first instant in time and the second instant in time are calculated. By comparing the difference in the various distances with the difference in the various distances of known healthy and/or leaking anastomoses, the healthcare provider may more accurately determine the existence of a leak and/or the potential for a leak to occur.

Figure 8A:
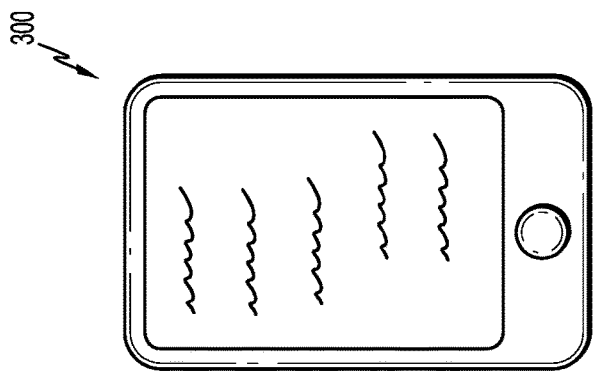
FIG. 8A is an enlarged view of the imagining device shown in FIG. 8.
Figure 8:
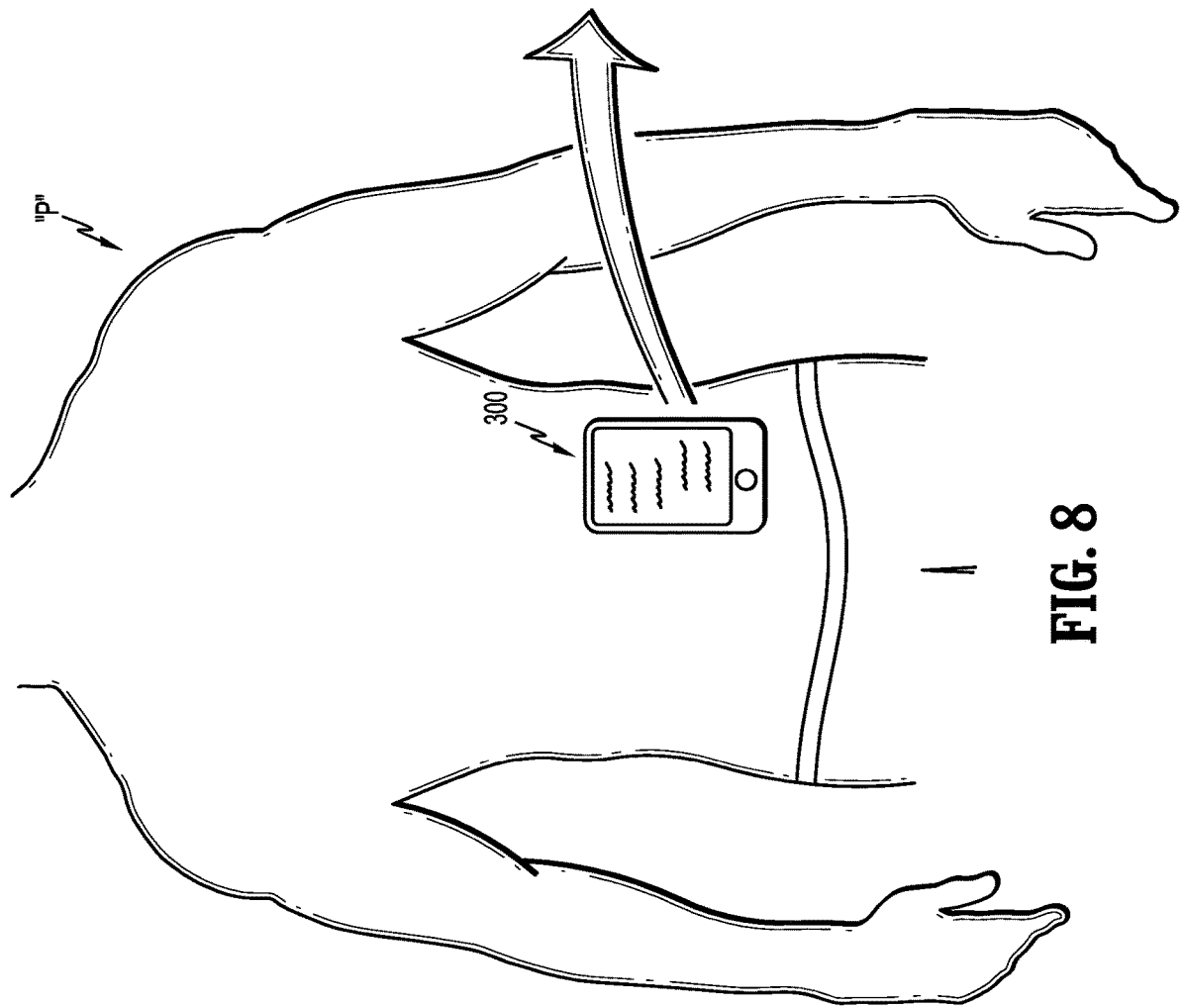
FIG. 8 is a schematic view of an imaging device according to a further aspect of the present disclosure affixed to a patient.
Figure 9:
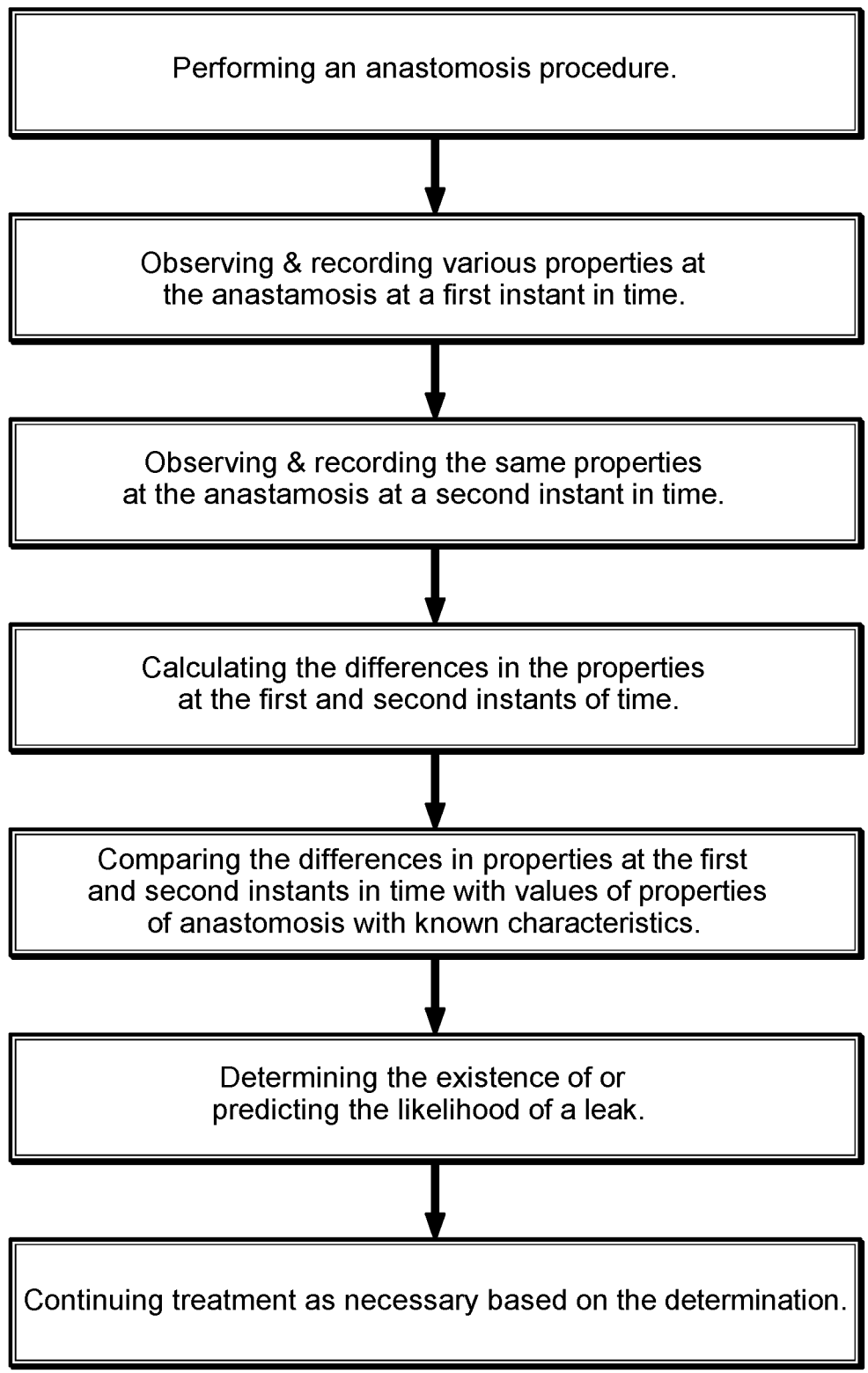
FIG. 9 is a flowchart indicating a method of detecting an anastomotic leak according to an aspect of the present disclosure.

It is envisioned that the position of the surgical staples "S" may be tracked with a GPS-like system. The GPS-like system may be located external to the patient body, e.g., superDimension™ navigation system, manufactured by Medtronic—Minneapolis, Minn. The system may contain software and graphical user interface components that reside on external hardware, e.g., monitor, or communicated remotely, e.g., handheld or wearable devices 300 FIGS. 8 and 8A). The external hardware may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

The software in these devices includes an algorithm that quantifies and displays the relative notions of the surgical staples "S" and/or staple lines "$S_1$", "$S_2$" with appropriate indexes, e.g., average staple distances, average relative motion of the staples and/or staple lines, average displacement, etc., of healthy and/or leaking anastomoses. If the value of the indexes exceeds and/or falls below a preset level, the software may communicate warning signals to the healthcare provider indicating the need for and/or lack thereof further patient treatment. Values falling within the indexes indicate that the anastomosis is healing properly and that no further treatment is necessary. It is envisioned that the monitoring of the anastomosis may be done by the patient at borne or monitored remotely by the healthcare provider Monitoring may be continuous or at spaced intervals. The spacing of the intervals may increase or decrease depending of the status of the healing process and known indicators.

Fi. 9 is a flowchart illustrating the above described method of monitoring the anastornosis "A". Following an anastomosis procedure, the anastomosis "A" is observed and the various properties of the surgical staples "S" and/or the staple lines "$S_1$", "$S_2$" are recorded. At a later instant in time, the same properties of the surgical staples "S" and/or staple lines "$S_1$", "$S_2$" are observed and recorded. The measurements from the first and second instants of time are then compared. These differences are then compared with values of the same properties of anastomoses with known characteristics, e.g., healthy anastomoses, anastomoses experience leakage. By comparing the measurements of the anastomosis "A" with the measurements of the anastomoses with known characteristics, a determination may be made as to whether a leak exists and a more accurate prediction of the potential for a leak may be made. Depending on the result of the determination, continued observation and/or treatment may be required.

Figure 10A:
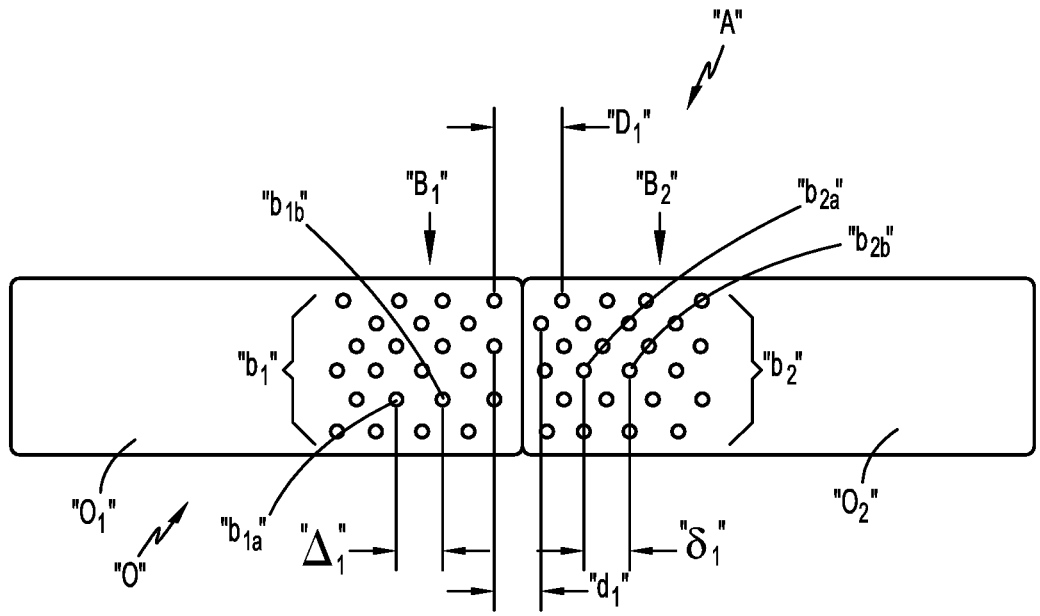
FIG. 10A is a side view of an anastomosis site according to an aspect of the present disclosure at a first instant in time.
Figure 10B:
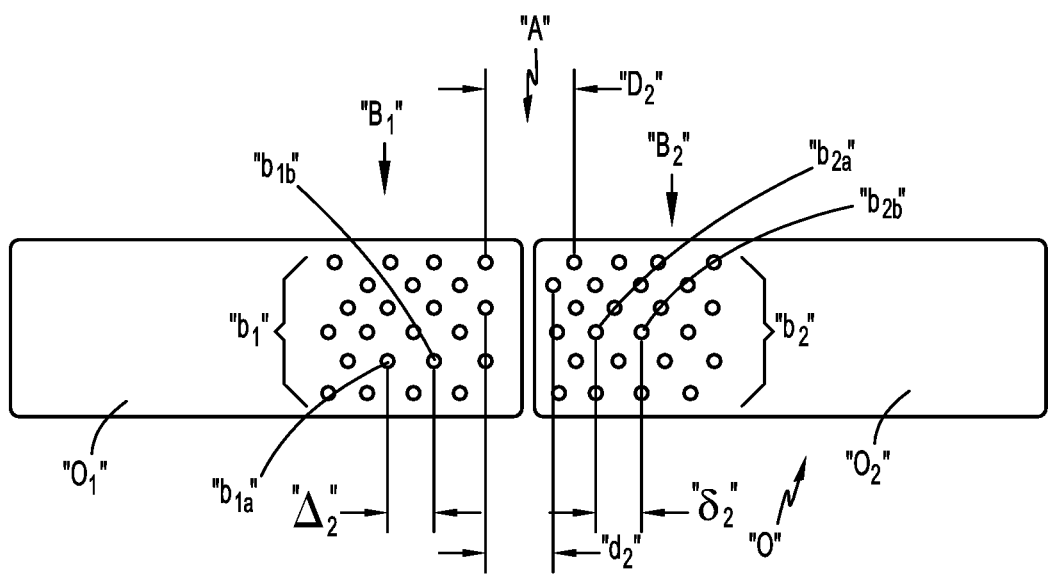
FIG. 10B is the perspective view of the anastomosis site shown in FIG. 10A at a second instant in time.

FIGS. 10A and 10B illustrate another method of monitoring an anastomosis "A". This method includes implanting, or otherwise securing a first set of beads "$B_1$" to a first portion "$O_1$" of a tubular organ "O" and a second set of beads "$B_2$" to a second portion "$O_2$" of the tubular organ "O". The beads "$b_1$", "$b_2$" of the respective first and second set of beads "$B_1$", "$B_2$" may be implanted directly into the tissue layers using known implantation devices (not shown). Alternatively, the beads "b" may be sutured, adhered, or otherwise secured to the tissue. The beads "$b_1$", "$b_2$" of the respective first and second set of beads "$B_1$", "$B_2$" may be implanted in a single row, in a scattered pattern (as shown), or in any other configuration, on either side of the anastomosis "A". Similar to surgical staples "S" described above, beads "$b_1$", "$b_2$" of the first and second sets of beads "$B_1$", "$B_2$", respectively, may include a coating or be otherwise configured to permit differentiation between the individual beads "$b_1$", "$b_2$" within each of the respective first and second sets of beads "$B_1$", "$B_2$" and/or between the individual beads "$b_1$" in the first set of beads "$B_1$" and the individual beads "$b_2$" in the second set of beads "$B_2$".

FIG. 10A illustrates a side view of the anastomosis "A" at a first instant in time following an anastomotic procedure. The first instant of time may be immediately following the anastomotic procedure or at any subsequent time during the healing process. The first instant in time may be immediately prior to, at a point during, or subsequent to peristalsis or contraction of the tubular organ "O".

At the first instant in time, the first and second first sets of beads "$B_1$", "$B_2$" are separated by a first distance "$d_1$" at a first location between the first and second sets of beads "$B_1$", "$B_2$", and are separated by a second distance "$D_1$" at a second location between the first and second sets of beads "$B_1$", "$B_2$". The distance between the first and second sets of beads "$B_1$", "$B_2$" may be taken at specific locations, e.g., between two identified beads, or an average distance may be taken between corresponding beads "$b_1$", "$b_2$" of the respective first and second sets of beads "$B_1$", "$B_2$" on each side of the anastomosis.

With continued reference to FIG. 10A, quantitative analysis of the anastomosis "A" may further include measuring and monitoring a third distance "$\Delta_1$" between first and second beads "$b_{1a}$", "$b_{1b}$" of the first set of beads "$B_1$" at the first instant in time and/or of a fourth distance "$\delta_1$" between first and second beads "$b_2a$", "$b_2b$" of the second set of beads "$B_2$" at the first instant in time.

FIG. 10B illustrates the side view of the anastomosis "A" at second instant of time. The second instant of time may be during the same stage of peristalsis and/or contraction of the tubular organ "O", at a later time, and/or at different stages of the peristalsis and/or contraction of the tubular organ "O".

A distance "$d_2$" between the first and second sets of beads "$B_1$", "$B_2$" at the first location and a distance "$D_2$" between the first and second sets of beads "$B_1$", "$B_2$" at the second location at the second instant in time may be the same or different than the first distance "$d_1$" at the first location and the second distance "$D_1$" at the second location measured at the first instant of time. By comparing the differences between the first and second distances "$d_1$", "$D_1$" at the first instant in time and the distances "$d_2$", "$D_2$", respectively, at the second instant in time with each other and with known values of the same measurements of properly healing anastomoses, a healthcare provider may more accurately determine the current state of the anastomosis and more accurately predict the likelihood that an anastomotic leak will occur.

A distance "$\Delta_2$" between the first and second beads "$b_{1a}$", "$b_{1b}$" of the first set of beads "$B_1$" and/or a distance "$\delta_2$" between the first and second beads "$b_2a$", "$b_2b$" of the second set of beads "$B_2$" at the second instant in time may be the same or different than the distances "$\Delta_1$", "$\delta_1$" between the respective first and second beads "$b_{1a}$", "$b_{1b}$" of the first set of beads "$B_1$" and the first and second beads "$b_2a$", "$b_2b$" of the second set of beads "$B_2$" at the first instant in time. As with the distances "$d_1$", "$d_2$", "$D_1$", "$D_2$", between the first and second sets of beads "$B_1$", "$B_2$" at the respective first and second locations at the first (FIG. 10A) and second (FIG. 10B) instants in time, respectively, the distances "$\Delta_1$", "$\Delta_2$", "$\delta_1$", "$\delta_2$" between the respective first and second beads "$b_{1a}$", "$b_{1b}$" of the first set of beads "$B_1$" and the first and second beads "$b_2a$", "$b_2b$" of the second set of beads "$B_2$" at the first (FIG. 10A) and second (FIG. 10B) instants of time, may be compared with each other and with known values of the same measurements of properly healing anastomoses to provide a healthcare provider with a more accurate evaluation of the current state of the anastomosis and provide for a more accurate prediction of the probability of anastomotic leak.

Another method of monitoring an anastomosis includes viewing the motion of staples within a staple line during a peristaltic event to provide feedback on the condition of the anastomosis. By analyzing the rate and/or direction of motion of one staple in a first staple line relative to another staple in a second staple line and/or the rate and/or direction of motion of the first and/or second staple lines during a peristaltic event, the condition anastomosis may be determined. A synchronous motion of the staples may indicate that the anastomosis is healing properly, while an asynchronous motion of the staples may indicate improper healing, e.g., a rip or discontinuity in the bowel. It is envisioned that patterns of the motion of the staples may be determined with $\Delta_1$ algorithms. It is further envisioned that the motion of the staples may be viewed and analyzed as a bolus of food moves through the bowels.

Figure 11A:
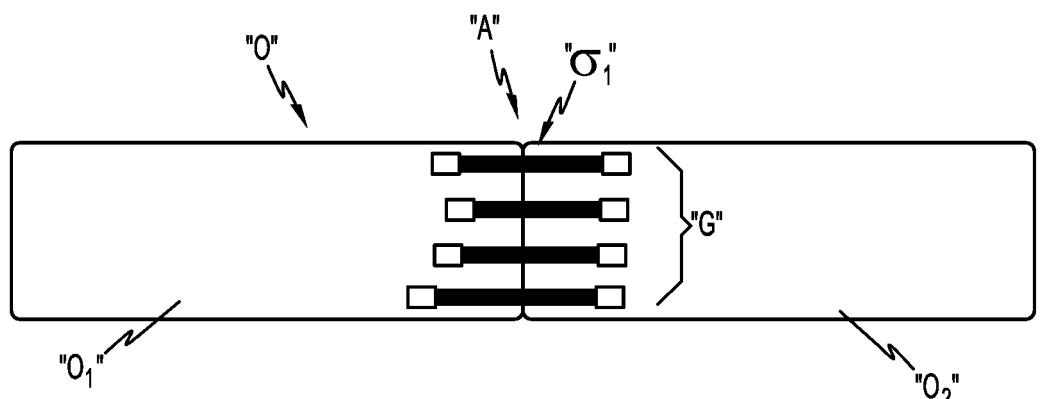
FIG. 11A is a perspective view of an anastomosis site according to an another aspect of the present disclosure at a first instant in time.
Figure 11B:
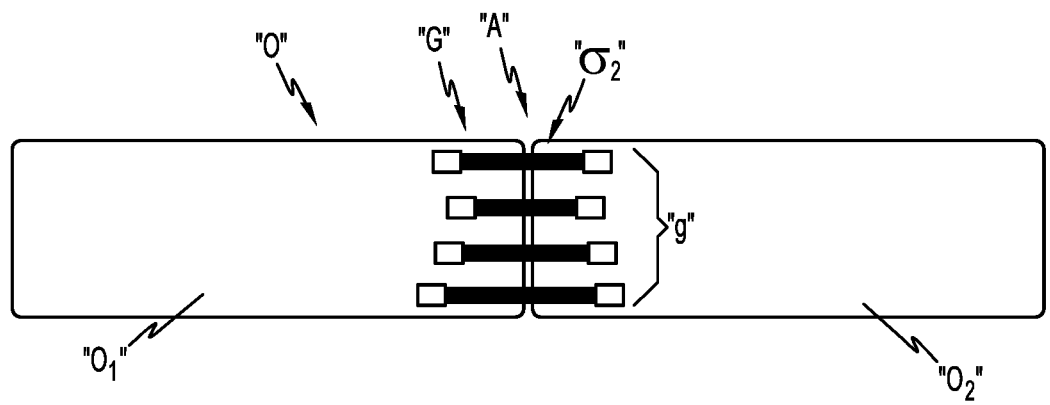
FIG. 11B is the perspective view of the anastomosis site shown in FIG. 11A at a second instant in time.

FIGS. 11A and 11B illustrate yet another method of monitoring an anastomosis "A". This method includes implanting a plurality of strain gauges "G" across the anastomosis "A". By measuring the strain "$\sigma_1$" experienced in the plurality of strain gauges "G" at a first instant in time (FIG. 11A) and/or the strain "$\sigma_2$" experienced in the plurality of strain gauges "G" at a second instant of time, and comparing the strains "$\sigma_1$", "$\sigma_2$" with each other or with known strains exhibited in properly healing anastomoses, and/or in anastomoses experiencing leakage, a more accurate evaluation of the current state of the anastomosis may be determined, and/or a more accurate prediction of the probability of anastomotic leak is possible.

The strains "$\sigma_1$", "$\sigma_2$" experienced in the plurality of strain gauges "G" at the first and second instants in time (FIG. 11A, FIG. 11B, respectively) may be a comparison of individual strain gauges "g" and/or a comparison of an average or median strain of some or all of the strain gauges "g" of the plurality of strain gauges "G". As detailed above with regards to the differences between the surgical staples "S" and/or the staple lines "$S_1$", "$S_2$" at the first and subsequent instants of time, the difference in the strains at the first and second instants of time may be compared with known values of healthy and/or leaking anastomosis and action may be taking accordingly.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A system for monitoring anastomosis healing, the system comprising:
   an imaging device for observing a first distance at a first location between first and second staple lines of an anastomosis at a first instant in time and a second distance at the first location at a second instant in time; and
   a programmable device configured to calculate a difference between the first and second distances, and to compare the difference with known distances of anastomoses exhibiting known conditions, to identify an anastomosis leak, and to communicate a warning signal when the anastomosis leak is detected, further including a monitor, wherein the warning signal is displayed on the monitor.

2. The system of claim 1, wherein the known conditions include healthy anastomoses.

3. The system of claim 1, wherein the known conditions include anastomoses exhibiting leakage.

4. The system of claim 1, wherein the imaging device is configured for observing a distance between first and second staples within the first staple line.

5. The system of claim 1, wherein the programmable device is configured to be worn by a patient.

6. The system of claim 1, wherein staples within the first staple line include a first coating.

7. The system of claim 6, wherein staples within the second staple line include a second coating different from the first coating.

8. The system of claim 1, wherein staples within the first staple line include at least one bead secured thereto.

9. The system of claim 1, wherein the imaging device uses at least one of x-rays, MRI, CT scan, or ultrasound.

10. The system of claim 1, wherein the programmable device is further configured to provide a proper course of treatment.

11. A method of monitoring anastomosis healing, the method comprising:
    observing a first distance between a first staple line of an anastomosis and a second staple line of the anastomosis at a first location at a first instant in time;
    observing a second distance between the first staple line and the second staple line at the first location at a second instant of time;
    calculating a difference between the first and second distances;
    comparing the difference between the first and second distances with values of measurements in anastomoses having known conditions;
    communicating a warning signal to indicate that an anastomosis leak is detected;
    determining a proper course of treatment based on the comparisons; and
    wherein communicating the warning signal includes displaying the warning signal on a monitor.

12. The method of claim 11, wherein the known conditions include healthy anastomoses.

13. The method of claim 11, wherein the known conditions include anastomoses exhibiting leakage.

14. The method of claim 11, wherein observing the first and second distances includes using x-rays, MRI, CT scan, or ultrasound.

15. The method of claim 11, wherein calculating the difference between the first and second distances includes using a programmable device.

16. The method of claim 11, further comprising observing a third distance between a first staple and a second staple in the first staple line at the first instant in time, observing a fourth distance between the first staple and the second staple at the second instant in time; and comparing a difference between the third and fourth distances with known differences between distances between staple lines of the anastomoses exhibiting known conditions.

* * * * *